United States Patent [19]

Maeda et al.

[11] 3,994,908
[45] Nov. 30, 1976

[54] SUBSTITUTED ACETIC ACID DERIVATIVES AND PRODUCTION THEREOF

[75] Inventors: Ryozo Maeda, Osaka; Katsumi Hirose, Nishinomiya, both of Japan

[73] Assignee: Shionogi & Co., Ltd., Japan

[22] Filed: Nov. 25, 1975

[21] Appl. No.: 635,253

Related U.S. Application Data

[62] Division of Ser. No. 360,065, May 14, 1973, Pat. No. 3,940,403.

[30] Foreign Application Priority Data

May 15, 1972 Japan.................. 47-48371

[52] U.S. Cl............................. 260/295 R; 424/263; 260/295.5 R
[51] Int. Cl.²..................................... C07D 213/55
[58] Field of Search............................. 260/295 R

[56] References Cited
UNITED STATES PATENTS

| | | | |
|---|---|---|---|
| 3,609,158 | 9/1971 | Torba | 260/295 |
| 3,655,679 | 4/1972 | Shen et al. | 260/295 |
| 3,862,952 | 1/1975 | Markley | 260/295 |

*Primary Examiner*—Norman A. Drezin
*Attorney, Agent, or Firm*—Wenderoth, Lind & Ponack

[57] ABSTRACT

Substituted acetic acid derivatives represented by the formula:

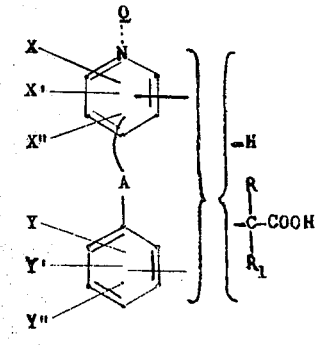

wherein X, X', X", Y, Y' and Y" each represents a hydrogen atom, an alkyl group of 1 to 8 carbon atoms, an alkoxy group of 1 to 8 carbon atoms, a hydroxy group, an acyl group, an acylamino group, an acyloxy group, an amino group, a cyano group, a nitro group, an alkoxycarbonyl group of 2 to 9 carbon atoms, an alkoxycarbonylalkyl group of 3 to 10 carbon atoms, an alkoxycarbonylamino group of 2 to 9 carbon atoms, a trifluoromethyl group, a halogen atom, a carboxy group, or a carbamoyl group, two of X, X' and X", or two of Y, Y' and Y" are optionally combined to form an alicyclic ring of 5 to 7 carbon atoms or a benzene ring, A represents an oxygen atom or a sulfur atom, R and $R_1$ each represents a hydrogen atom or a lower alkyl group of 1 to 4 carbon atoms and Q represents the optional presence of an oxygen atom, or their alkali metal or alkali earth metal salts, being useful as anti-inflammatory, anti-rheumatic, analgesic or anti-pyretic agents, are prepared essentially by the Arndt-Eistert reaction.

8 Claims, No Drawings

SUBSTITUTED ACETIC ACID DERIVATIVES AND PRODUCTION THEREOF

This is a division of application Ser. No. 360,065, filed May 14, 1973, now U.S. Pat. No. 3,940,403.

The present invention relates to substituted acetic acid derivatives and production thereof. More particularly, this invention relates to substituted acetic acid derivatives or their alkali metal or alkali earth metal salts, being useful as anti-inflammatory, anti-rheumatic, analgesic or anti-pyretic agents, and production thereof.

The said substituted acetic acid derivatives are represented by the formula:

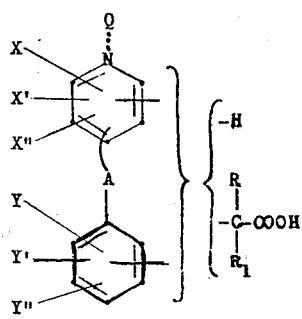

(I)

wherein X, X', X'', Y, Y' and Y'' each represents a hydrogen atom, an alkyl group of 1 to 8 carbon atoms (e.g., methyl, ethyl, isopropyl, n-amyl), an alkoxy group of 1 to 8 carbon atoms (e.g., methoxy, ethoxy, n-propoxy, isohexyloxy), a hydroxy group, an acyl group (e.g., acetyl, n-propionyl, benzoyl), an acylamino group (e.g., acetylamino, n-propionylamino, benzoylamino), an acyloxy group (e.g., acetyloxy, propionyloxy, benzoyloxy), an amino group, a cyano group, a nitro group, an alkoxycarbonyl group of 2 to 9 carbon atoms (e.g., methoxycarbonyl, ethoxycarbonyl, n-butoxycarbonyl), an alkoxycarbonylalkyl group of 3 to 10 carbon atoms (e.g., methoxycarbonylethyl, ethoxycarbonylpropyl, n-butoxycarbonylmethyl), an alkoxycarbonylamino group of 2 to 9 carbon atoms (e.g., methoxycarbonylamino, ethoxycarbonylamino, n-butoxycarbonylamino), a trifluoromethyl group, a halogen atom (e.g., chlorine, bromine, iodine), a carboxy group, or a carbamoyl group, two of X, X' and X'' or two of Y, Y' and Y'' are optionally combined to form an alicyclic ring of 5 to 7 carbon atoms or a benzene ring, A represents an oxygen atom or a sulfur atom, R and $R_1$ each represents a hydrogen atom or a lower alkyl group of 1 to 4 carbon atoms (e.g., methyl, ethyl, propyl), and Q represents the optional presence of an oxygen atom.

The said compounds (I) consists of Ia, Ib, Ic and Id and can be prepared according to the following scheme:

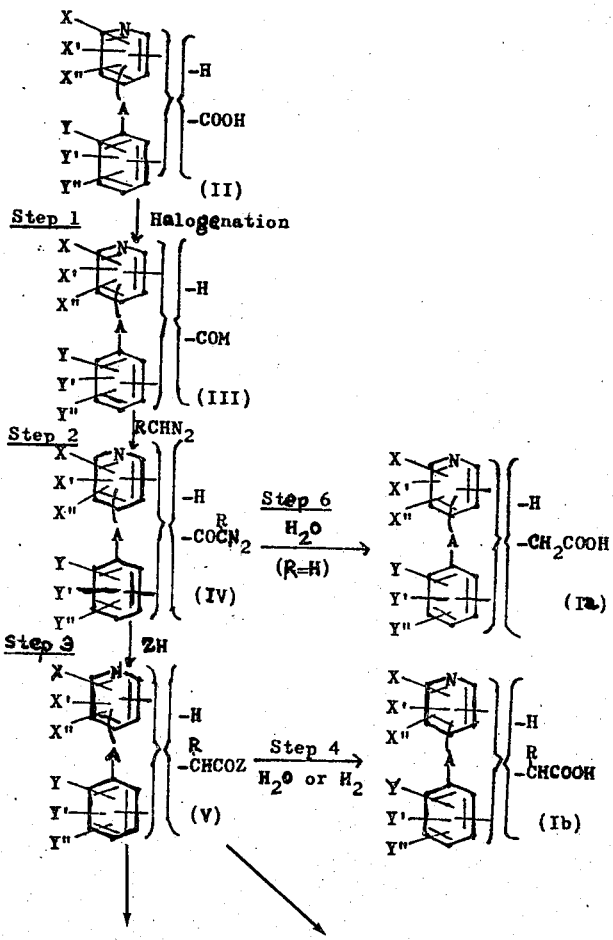

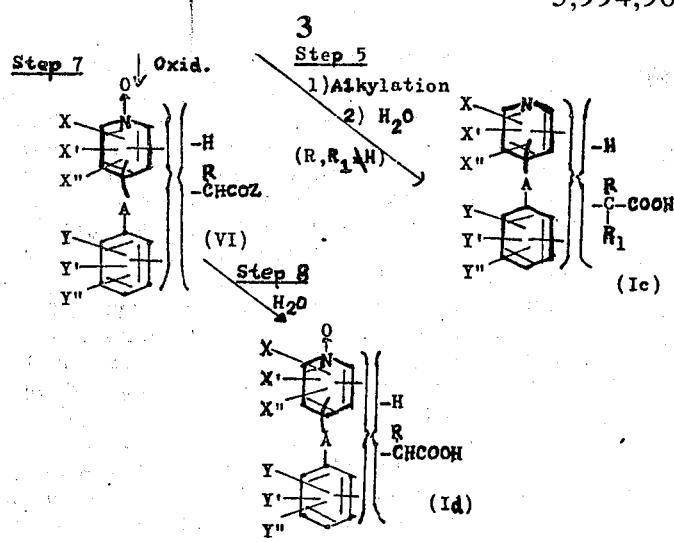

wherein M represents a halogen atom (e.g., chlorine, bromine) and Z represents an alkoxy group of 1 to 8 carbon atoms (e.g., methoxy, ethoxy, propoxy, n-butoxy), an aralkyloxy group of 7 to 18 carbon atoms (e.g., benzyloxy, phenethyloxy), or an anilino group, and X, X', X'', Y, Y', Y'', R and $R_1$ each is as defined above. The process of this invention includes Steps 1 to 8.

The starting carboxy compound (II) can be prepared by hydrolyzing the corresponding nitrile or ester compound, or by adopting the oxidation of a methyl group. For example, 2-phenoxyisonicotinic acid is prepared by oxidizing 2-phenoxy-γ-picoline, as well known.

Step 1 of the invention can be effected by treating the starting carboxy compound (II) with a halogenating agent. Examples of the halogenating agent are thionyl chloride, phosphorus trichloride, phosphorus oxychloride, phosphorus pentachloride, and phosphorus tribromide. The reaction may be effected in the presence or absence of an inert solvent (e.g., carbon tetrachloride, chloroform) at room temperature or under heating or cooling. A catalyst such as dimethylformamide may be added, if necessary. After the end of the reaction, the reaction mixture may be optionally treated with a base (e.g., pyridine, triethylamine, dimethylaniline).

Step 2 can be effected by reacting the carbonyl halide compound (III) above obtained with a diazoalkane (e.g., diazomethane, diazoethane, diazopropane, diazoisobutane). The reaction may be ordinarily effected in the presence of an inert solvent such as an ether (e.g., diethyl ether, tetrahydrofuran, diglyme), a hydrocarbon (e.g., benzene, toluene, n-hexane), a halogenohydrocarbon (e.g., chloroform, carbon tetrachloride, methylene chloride), dimethylformamide, or a mixture thereof under cooling or at room temperature, if necessary, with mild heating.

Step 3 can be effected by reacting the diazoalkanoyl compound (IV) above obtained with an alcohol (e.g., methanol, ethanol, isopropanol, n-amyl alcohol, benzyl alcohol, phenethyl alcohol) or aniline. This reaction may be effected in the presence or absence of a catalyst such as silver (e.g., as a combination of silver benzoate and triethylamine) or silver oxide, or under irradiation of the ultra-violet light with or without an inert solvent (e.g., γ-collidine, dioxane, tetrahydrofuran, diglyme, dimethylformamide, dimethylsulfoxide, a mixture of 2 or more thereof) at room temperature or under heating.

Step 4 can be effected by hydrolyzing or hydrogenolyzing the ester or anilide compound (V) above obtained. The hydrolysis may be effected by treating with an acid such as an inorganic acid (e.g., hydrochloric acid, sulfuric acid, hydrobromic acid) or an organic acid (e.g., acetic acid), or an alkali (e.g., alkali hydroxide, alkali carbonate, alkali bicarbonate), preferably alcoholic alkali hydroxide (e.g., ethanol/potassium hydroxide) at room temperature or under heating. Still, the hydrogenolysis may be effected in the presence of a catalyst for catalytic reduction (e.g., palladium carbon, palladium black, palladium oxide, Raney nickel) in an inert solvent such as an alcohol (e.g., methanol, ethanol), an ether (e.g., tetrahydrofuran, diglyme), a hydrocarbon (e.g., benzene, toluene), acetic acid or ethyl acetate at room temperature or under heating in a hydrogen atmosphere in a conventional manner, if necessary, under compressed pressure. When a group being very susceptible to hydrolysis or hydrogenolysis such as alkoxycarbonyl group or acyloxy group exists as the substituent (i.e., X, X', X'', Y, Y', Y''), benzyl alcohol is preferred in Step 3 to give the benzyl ester group more susceptible to hydrogenolysis than alkoxycarbonyl or acyloxy group and then the ester can be selectively hydrogenolyzed to substitute only the benzyl group by a hydrogen atom while keeping the alkoxycarbonyl group or acyloxy group in Step 4. Thus, mono- or di-substituted acetic acid (Ib) is obtained.

Step 5 consists of alkylation and hydrolysis. The alkylation can be effected by reacting the ester (V) obtained in Step 3 with an alkyl halide (e.g., methyl iodide, ethyl bromide, isopropyl iodide) in the presence of a base (e.g., sodium hydride, potassium hydride, potassium t-butoxide, sodium amide) in an inert solvent (e.g., diethyl ether, benzene, toluene, tetrahydrofuran, liquid ammonia, t-butyl alcohol) at room temperature or under cooling or heating. Then, thus-obtained alkylated ester can be hydrolyzed as in Step 4 to give the tri-substituted acetic acid (Ic: R, $R_1$ H).

Step 6 can be effected by reacting the diazoacetyl compound (IV: R=H) with water. This reaction may be effected in the presence or absence of a catalyst such as silver (e.g., as a combination of silver benzoate and triethylamine) or silver oxide, or under irradiation of the ultra-violet light with or without an inert solvent (e.g., γ-collidine, dioxane, tetrahydrofuran, diglyme, dimethylformamide, dimethylsulfoxide, a mixture of 2 or more thereof) at room temperature or under heating. Thus, mono-substituted acetic acid (Ia) is obtained.

Step 7 can be effected by oxidizing the ester (V) obtained in Step 3 with hydrogen peroxide or a peracid (e.g., peracetic acid, perbenzoic acid, m-chloroperbenzoic acid). The reaction may be effected in an inert solvent (e.g., methanol, acetic acid, chloroform, methylene chloride) at room temperature or under cooling or heating. Thus, the N-oxide compound (VI) is obtained.

Step 8 can be effected by hydrolyzing the N-oxide compound (VI) above obtained. The hydrolysis may be effected by treating with an acid such as an inorganic acid (e.g., hydrochloric acid, sulfuric acid, hydrobromic acid) or an organic acid (e.g., acetic acid), or an alkali (e.g., alkali hydroxide, alkali carbonate, alkali bicarbonate), preferably alcoholic alkali hydroxide (e.g., ethanol/potassium hydroxide) at room temperature or under heating. Thus, the mono- or di-substituted acetic acid (Id) is obtained.

Thus-obtained substituted acetic acid derivatives (I: Ia, Ib, Ic, Id) can be converted into their suitable alkali metal salt (e.g., sodium salt, potassium salt), alkali earth metal salt (e.g., calcium salt, magnesium salt, barium salt) or other salts (e.g., aluminum) in a conventional manner according to requirement of the separation, purification or formulation.

These substituted acetic acid derivatives (I) or their salts are useful as anti-inflammatory, anti-rheumatic, analgesic or antipyretic agents. For example, the anti-erythema activity ($ED_{50}$, mg/kg), the anti-edema activity ($ED_{30}$, mg/kg) and the acute toxicity ($LD_{50}$, mg/kg) of some substituted acetic acid derivatives (I) according to the present invention are shown in the following Table I:

| Compound | Anti-erythema activity (Guinea pig, oral; $ED_{50}$, mg/kg) | Anti-edema activity (Rat,oral; $ED_{50}$,mg/kg) | Acute Toxicity (Mouse,oral; $LD_{50}$,mg/kg) |
| --- | --- | --- | --- |
| Aspirin | 79 | 48 | 1998 |
| Phenylbutazone | 26 | 48 | 1414 |
| Calcium bis[2-(2-phenoxy-5-pyridyl)-propionate] | 21 | 8 | 1645 |
| Calcium bis[2-(2-phenoxy-4-pyridyl)-propionate] | 47 | 16 | 2248 |
| 2-(2-p-Chlorophenoxy-5-pyridyl)-propionic acid | 19 | 6.5 | 1153 |

Note:
The anti-erythema activity was observed by the Wilhelmi method [Wilhelmi,g.,(1949), Schweiz.Med.Wehnschr.,79, 577]. The anti-edema activity was observed by the Benitz method [Benitz, K.F. et al., (1963), Arch. int. Pharmacodyn.,144, 185-195]. The toxicity was tested by the oral administration of the tested compound to mice.

The products (I) are useful for the treatment of various rheumatic diseases, inflammations, fevers or painful conditions solely or in combination with a solid or liquid pharmaceutical excipient. Practical examples of suitable pharmaceutical preparations with the products (I) are tablets, capsules, pills, granules, powders, or suppositories. In general, the dosage of these products (I) is in the order of the same to one tenth of the practical dosage of phenylbutazone. The compositions containing the products (I) can be dispensed in dosage unit forms for a single daily therapeutic dose, in smaller units for multiple doses, or in larger units for dividing into single doses.

Presently preferred and practical embodiments of the present invention are illustratively shown by the following examples. Temperatures are given in degrees centigrade.

EXAMPLE 1

1. To thionyl chloride (3 ml), a mixture of 2-phenoxy-5-ethoxycarbonylethylisonicotinic acid (1.0 g) and dimethylformamide (a small amount) is added, and the resultant mixture is stirred at room temperature for 20 minutes. The reaction mixture is evaporated under reduced pressure to remove the thionyl chloride. The residue is mixed with dry benzene and evaporated again. The residue is dissolved in anhydrous ether, and the insoluble part is filtered off. The ether solution is evaporated to give 2-phenoxy-5-ethoxycarbonylethylisonicotinoyl chloride (1.05g). IR (CHCl$_3$): 1775, 1735 cm$^{-1}$.

2. To an ethereal solution of diazomethane prepared from nitrosomethylurea (2.0 g) and ether (25 ml), a solution of the said 2-phenoxy-5-ethoxycarbonylethylisonicotinoyl chloride (1.05 g) in anhydrous ether (10 ml) is added dropwise at 0° to 3° C, and the resultant mixture is stirred at 10° to 15° C for 1 hour. The reaction mixture is evaporated under reduced pressure to remove the ether. The residue is chromatographed on a column of neutral alumina/50 % benzene-n-hexane, whereby 2-phenoxy-4-diazoacetyl-5-ethoxycarbonylethylpyridine (830 mg) is obtained. This substance is recrystallized from ether/n-hexane to give crystals melting at 77° to 79° C (decomp.). IR (CCl$_4$): 2120, 1745 cm$^{-1}$.

3. To a solution of 2-phenoxy-4-diazoacetyl-5-ethoxycarbonylethylpyridine (715 mg) in absolute ethanol (10 ml), a mixture of silver benzoate (25 mg) and triethylamine (210 mg) is added, and the resultant mixture is stirred at 60° to 65° C for 20 minutes. The reaction mixture is filtered to remove the insoluble substance, and the filtrate is evaporated to remove the solvent. The residue is chromatographed on a column of alumina/50 % benzene-n-hexane, whereby 2-phenoxy-4-ethoxycarbonylmethyl-5-ethoxycarbonylethylpyridine (630 mg) is obtained as an oil. IR (CCl$_4$): 1750 cm$^{-1}$.

4. To 5 % potassium hydroxide/ethanol solution (10 ml), 2-phenoxy-4-ethoxycarbonylmethyl-5-ethoxycarbonylethylpyridine (1.0 g) is added, and the resultant mixture is stirred at room temperature for 2 hours. The reaction mixture is evaporated under reduced pressure to remove the solvent. The residue is dissolved in a small amount of water, made acidic with hydrochloric acid and the precipitated crystals are filtered. This substance is recrystallized from acetone to give 2-phenoxy-5-carboxyethylpyridyl-4-acetic acid (0.8 g) as crystals melting at 143° C (decomp.).

EXAMPLE 2

1. Using 2-phenoxy-5-methoxycarbonylethylisonicotinic acid (500 mg), the reaction is effected as in Example 1 (1), whereby 2-phenoxy-5-methoxycarbonylethylisonicotinoyl chloride (537 mg). IR (CHCl$_3$): 1775, 1745 cm$^{-1}$.

2. The above product (537 mg) is treated as in Example 1 (2), to give 2-phenoxy-4-diazoacetyl-5-methoxycarbonylethylpyridine (427 mg). IR (CCl$_4$): 2120, 1750 cm$^{-1}$.

3. To a suspension of silver oxide (prepared from 100 mg of silver nitrate) in absolute methanol (12 ml), a solution of the above product (427 mg) in anhydrous methanol (6 ml) is added dropwise at 60° to 65° C with stirring, and the resultant mixture is refluxed with heating for 1 hour. Then, silver oxide in the same amount is added, and the mixture is refluxed for 2 hours. The reaction mixture is treated as in Example 1 (3) to give 2-phenoxy-4-methoxycarbonylmethyl-5-methoxycarbonylethylpyridine (196 mg). This substance is recrystallized from n-hexane to give crystals melting at 73.5° to 74° C.

4. The above product (1.0 g) is treated as in Example 1 (4) to give 2-phenoxy-5-carboxyethylpyridine-4-acetic acid (0.8 g) as crystals melting at 143° C (decomp.).

(1.80 g) in thionyl chloride (5.4 ml), dimethylformamide (0.2 ml) is added, and the resultant mixture is stirred at room temperature for 2.5 hours. The reaction mixture is evaporated under reduced pressure to remove the excessive thionyl chloride, and the residue is combined with anhydrous pyridine (0.73 g) and anhydrous benzene (40 ml). The precipitated pyridine hydrochloride is filtered off. The filtrate is evaporated to remove the benzene, and the residue is dissolved in anhydrous ether (20 ml). The ether solution is filtered

| Example No. | I Y | m.p. | II m.p.(IR) | III m.p. | IV Z | m.p.(IR) | V m.p. | IR |
|---|---|---|---|---|---|---|---|---|
| 3 | H | 248 | 69-70 | 87-88d | Eto | 58-59 | 93-94d | 1730 Nu |
| 4 | 4-Cl | 236-7 | 46-47 | 129-130d | Eto | 50-51 | 152-153d | 1730 Nu |
| 5 | 3-Cl | 235 | 1773 CCl | 64-65d | Bzo | 1745 CCl | 123-124d | 1720 Chl |
| 6 | 2-Cl | 232-4 | 1770 CCl | 84-85d | Bzo | 1745 CCl | 133-134d | 1720 Chl |

Note:
The abbreviated signs are as following: m.p., melting point (° C); IR, infra red absorption spectre (cm$^{-1}$); Eto, ethoxy group; Bzo, benzyloxy group; Nu, Nujol; CCl, carbon tetrachloride; Chl, chloroform; d, decomposing point (each sign hereinafter has the same meaning as above).

EXAMPLE 3 TO 6

Using the following starting materials, the reaction is effected as in Example 1 to give the corresponding products. But benzyl alcohol is used as an alcohol compound in the third step of Examples 5 and 6, and the reaction is effected at about 180° C for 3 to 30 minutes in the presence of γ-collidine in lieu of triethylamine and silver benzoate.

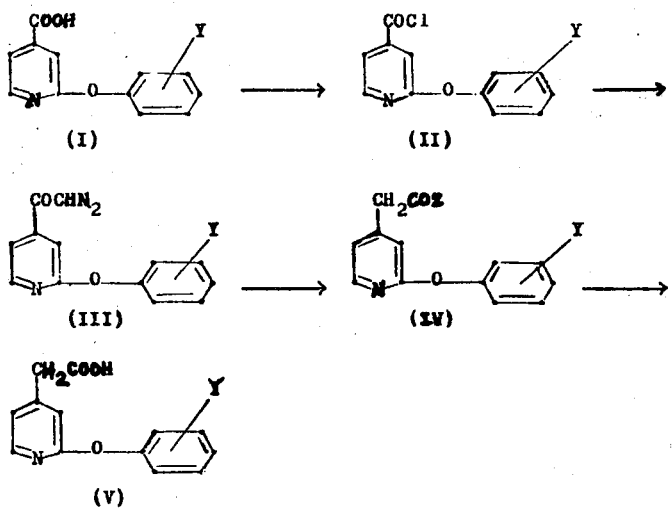

The reactions are effected as above, whereby the following compounds are obtained:

2-(2-p-chlorophenoxy-5-pyridyl)acetic acid, m.p. 116°-117° C;

2-(2-phenoxy-5-pyridyl)acetic acid, m.p. 83.5°-85° C; and

2-[2-(2,3-xylyloxy)-5-pyridyl]acetic acid, m.p. 120°-121° C.

EXAMPLE 7

1. To a suspension of 3-(2-pyridyloxy)benzoic acid to remove the insoluble substance. The filtrate is evaporated to remove the ether, whereby 3-(2-pyridyloxy)-benzoyl chloride is obtained. IR (CCl$_4$): 1774 cm$^{-1}$.

2. To the 3-(2-pyridyloxy)benzoyl chloride, a solution of diazomethane in ether is added, and the resultant mixture is treated as in Example 1 (2) to give 3-(2-pyridyloxy)-1-diazoacetylbenzene (1.63 g) as crystals melting at 85° to 87° C (decomp.).

3. 3-(2-Pyridyloxy)-1-diazoacetylbenzene (2.03 g), benzyl alcohol (10 ml) and γ-collidine (10 ml) are stirred at 180° C for 30 minutes. After cooling, the reaction mixture is mixed with ether, and shaken with 5 % hydrochloric acid to shift the γ-collidine hydrocyloride into the aqueous layer. The ether layer is evaporated to remove the ether and excessive benzyl alcohol. Thus, benzyl 3-(2-pyridyloxy)phenylacetate is obtained as a residue. IR (CCl$_4$): 1747 cm$^{-1}$. This substance is provided for the next step without purification as it is.

4. To the above obtained benzyl 3-(2-pyridyloxy)-phenylacetate, 50 % potassium hydroxide solution (10 ml) and methanol (10 ml) are added, and the resultant mixture is allowed to stand at room temperature overnight. The reaction mixture is evaporated to remove the methanol. The residue is dissolved in a small amount of water. The aqueous layer is adjusted to pH 3 with hydrochloric acid and shaken with ether. The ether layer is evaporated to remove the solvent, whereby 3-(2-pyridyloxy)phenylacetic acid (1.94 g) is obtained. This substance is recrystallized from ether to give crystals melting at 110° to 111° C.

EXAMPLE 8

1. Using 3-(2-pyridyloxy)benzoic acid (3.0 g), the reaction is effected as in Example 7 (1) to give 3-(2-pyridyloxy) benzoyl chloride. IR (CCl$_4$): 1774 cm$^{-1}$.

2. To a solution of diazoethane (2.5 mol equivalent) in ether (150 ml), a solution of 3-(2-pyridyloxy)benzoyl chloride in anhydrous ether (90 ml) is added dropwise at −20° C for 40 minutes. The resultant mixture is stirred at −20° C for 20 minutes. The diazoethane is evaporated at −20° C under reduced pressure, and the ether is evaporated at −10° C to 0° C under reduced pressure. The residue is chromatographed on a column of silica gel, which is eluted with 20 % ether/benzene and 30 % ether/benzene to give 3-(2-pyridyloxy)-1-(2-diazopropionyl)benzene (2.87 g) as an oily substance. IR (CCl$_4$): 2060, 1630 cm$^{-1}$.

3. A mixture of 3-(2-pyridyloxy)-1-(2-diazopropionyl)benzene (2.87 g), benzyl alcohol (14.5 ml) and γ-collidine (11.0 g) is stirred at 170° C for 7 minutes. The reaction mixture is dissolved in ether (50 ml), washed with N-hydrochloric acid and water in order, and the ether is evaporated. Thus, benzyl 2-(2-pyridyloxy-3-phenyl)propionate is obtained as a residue. This substance is provided for the following step without purification.

4. Benzoyl 2-(2-pyridyloxy-3-phenyl)propionate is dissolved in a mixture of 30 % aqueous potassium hydroxide solution (18 ml) and methanol (18 ml), and the solution is allowed to stand at room temperature for 1 hour. The reaction mixture is treated as in Example 7 (4) to give 2-(2-pyridyloxy-3-phenyl)propionic acid (2.30 g). This substance is recrystallized from benzene/n-hexane to give crystals melting at 76° to 77° C. IR (CHCl$_3$): 1715 cm$^{-1}$.

EXAMPLE 9 TO 25

Using the following starting materials, the reaction is effected as in Example 8 to give the corresponding products.

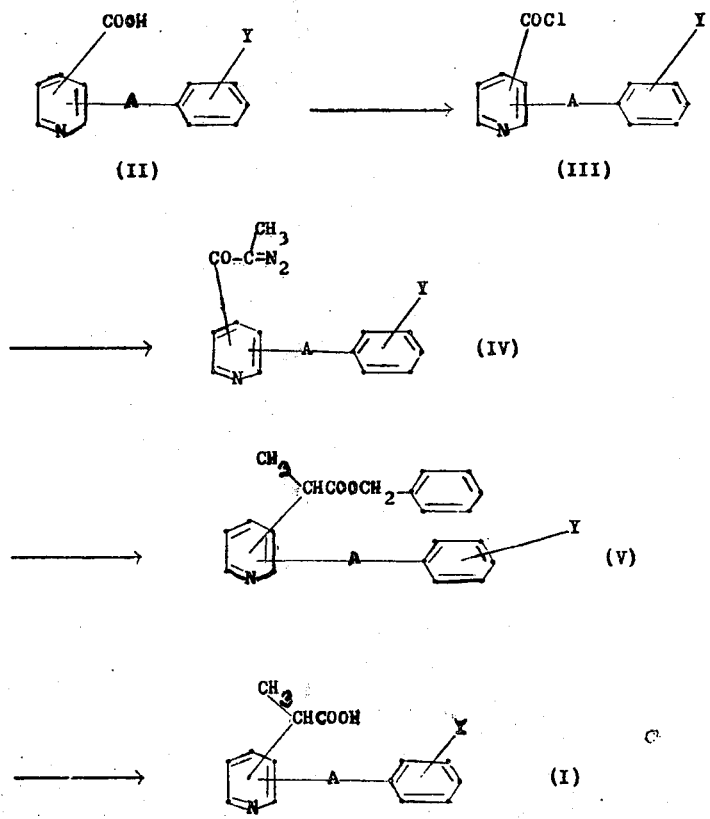

| Example No. | Position of COOH | A | Y | II m.p. | III m.p. or IR | IV m.p. or IR | I m.p. | IR |
|---|---|---|---|---|---|---|---|---|
| 9 | 4 | 2-O | 4-Cl | 236–237 | 46–47 | 117–8d | 119–120d | 1720 Chl |

-continued

| Example No. | Position of COOH | II A | Y | m.p. | III m.p. or IR | IV m.p. or IR | I m.p. | IR |
|---|---|---|---|---|---|---|---|---|
| 10 | 4 | 2-O | 3-Cl | 233–235 | 1773 CCl | 2070, 1633 CCl | 84–85d | 1735 Nu |
| 11 | 4 | 2-O | 2-Cl | 232–234 | 90 91 | 78 78.5d | 107.5 108.5d | 1720 Chl |
| 12 | 4 | 2-O | H | 248 | 69–70 | 47–49d | 98–99d | 1720 Chl 1715 |
| 13 | 3 | 2-O | H | 181–182 | 89–91 | 104d | 94–95 | 1720 Nu |
| 14 | 3 | 2-O | 4-Cl | 157–158 | 63–65 | 2060 CCl 1615 | 110–111 | 1720 Nu |
| 15 | 3 | 6-O | H | 166–167 | 1777 CCl | 2070 CCl | 92–93 | 1698 Nu |
| 16 | 3 | 6-O | 4-Cl | 170–171 | 1781 CCl | 75–76d | 114–115 | 1715 Nu |
| 17 | 2 | 6-O | H | 103–104 | 1770 CCl | 80–8025d | 135–136 Ca | 1590 Nu 1765 |
| 18 | 2 | 6-O | 4-Cl | 117–118 | 67–70 | 65–66d | 80–81d | 1720 Nu |
| 19 | 4 | 2-O | 4-Met | 235–236 | 1775 CCl | 103 103.5d 105.5 | 129–130d | 1715 Nu |
| 20 | 4 | 2-O | 4-Me | 256–257 | 60–62 | 106.5d | 101–102d | 1725 Nu |
| 21 | 4 | 2-S | H | 255 | 1775 CCl | 2070 1630 CCl | 140–141 Ca | 1570 Nu |
| 22 | 4 | 2-S | 4-Cl | 254–255 | 1770 CCl | 80–81d | 64–65Al | 1590 Nu |
| 23 | 3 | 6-O | 4-Met | 174–175 | 1778 CCl | 2060 1630 CCl 1615 | 155 Ca | 1585 Nu |
| 24 | 3 | 6-O | 4-Me | 158–160 | 1778 CCl | 2060 1630 CCl 1615 | 98 99 | 1700 Nu |
| 25 | 3 | 6-S | H | 162–163 | 76–77 | 2060 1625 CCl 1610 | 114.5 115.5 | 1697 Nu |

Note:
d, decomposing point (° C); Al, aluminum salt; Ca, calcium salt; Met, methoxy group; Me, methyl group.

EXAMPLE 26 TO 35

The reactions are effected as in Example 8, whereby the following products are obtained:

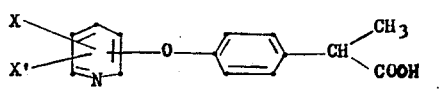

| Example No. | Position of phenoxy group | X | X' | m.p.(° C) |
|---|---|---|---|---|
| 26 | 2 | 5-Br | H | 137–138 |
| 27 | 2 | 5-CH | H | 198–200 |
| 28 | 2 | 5-CONH₂ | H | 211–212 |
| 29 | 3 | H | H | 130–131 |
| 30 | 4 | H | H | 180–181 |
| 31 | 2 | 3,4-(CH₂)₄- | | 166–167 |
| 32 | 2 | 3,4-Benzo | | 145–147 |
| 33 | 2 | 3-Me | 4-Me | 155.5–156 |
| 34 | 2 | 4-Me | 5-Me | 142–143 |

-continued

| Example No. | Position of phenoxy group | X | X' | m.p.(° C) |
|---|---|---|---|---|
| 35 | 2 | 4-Me | H | 123–124 |

EXAMPLE 36

1. Using 4-(2-pyridyloxy)benzoic acid (5.0 g), the reaction is effected as in Example 8 (1) to give 4-(2-pyridyloxy)benzoyl chloride as crystals melting at 78° to 79° C. IR (CCl₄): 1779, 1750, 1600, 1586 cm⁻¹.

2. To a solution of 4-(2-pyridyloxy)benzoyl chloride in ether, a solution of diazoethane in ether is added dropwise, and the reaction is effected as in Example 8 (2) to give 4-(2-pyridyloxy)-1-(2-diazopropionyl)benzene (4.72 g). This substance is recrystallized from ethyl acetate to give crystals melting at 101° to 102° C (decomp.). IR (CCl₄): 2070, 1630, 1590 cm⁻¹.

3. A mixture of 4-(2-pyridyloxy)-1-(2-diazopropionyl)benzene (4.5 g), benzyl alcohol (22.5 ml) and γ-collidine (22.5 ml) is stirred at 180° C for 15 minutes. The reaction mixture is treated as in Example 8 (3) to give benzyl 2-(2-pyridyloxy-4-phenyl)propionate. This substance is provided for the following step without purification.

4. To the above benzyl 2-(2-pyridyloxy-4-phenyl)-propionate, 50 % aqueous potassium hydroxide solution (22.5 ml) and methanol (22.5 ml) are added, and the resultant mixture is allowed to stand for 2 hours. The reaction mixture is treated as in Example 7 (4) to give 2-(2-pyridyloxy-4-phenyl)propionic acid (3.0 g). This substance is recrystallized from ethyl acetate to give crystals melting at 129° to 130° C. IR (Nujol): 2480, 1940, 1715, 1596, 1577 cm$^{-1}$.

EXAMPLE 37

1. Using 3-(2-pyridyloxy)benzoic acid, the reaction is effected as in Example 7 (1) and (2), whereby 3-(2-pyridyloxy)-1-diazoacetylbenzene is obtained as crystals melting at 85° to 87° C via 3-(2-pyridyloxy)benzoyl chloride.

2. To a solution of 3-(2-pyridyloxy)-1-diazoacetyl-benzene (2.0 g) in a mixture of dioxane (15 ml) and water (15 ml), freshly prepared silver oxide (500 mg) is added in every 30 minutes by 3 portions at 70° to 80° C with vigorous stirring. When the generation of nitrogen gas is stopped, the reaction mixture is mixed with 2 N aqueous sodium hydroxide solution (10 ml) and active carbon (500 mg) and filtered to remove the insoluble part. The filtrate is adjusted to pH 3 with hydrochloric acid and shaken with ether. The ether layer is evaporated to remove the solvent, whereby 3-(2-pyridyloxy)-phenylacetic acid (1.2 g) is obtained. This substance is recrystallized from ether to give crystals melting at 110° to 111° C.

EXAMPLE 38

1. Using 3-(2-pyridyloxy)benzoic acid, the reaction is effected as in Example 8 (1), (2) and (3), whereby benzyl 2-(2-pyridyloxy-3-phenyl)propionate is obtained via 3-(2-pyridyloxy)benzoyl chloride and 3-(2-pyridyloxy)-1-(2-diazopropionyl)benzene. IR (CCl$_4$): 1747 cm$^{-1}$.

2. To a solution of benzyl 2-(2-pyridyloxy-3-phenyl)-propionate (2.7 g) in ethanol (30 ml), 5 % palladium carbon (200 ml) is added, and the resultant mixture is shaken at room temperature in a hydrogen atmosphere. When the absorption of hydrogen is stopped, the catalyst is filtered off, and the filtrate is evaporated under reduced pressure to remove the solvent. The residue is recrystallized from benzene/n-hexane to give 2-(2-pyridyloxy-3-phenyl)propionic acid (1.4 g) as crystals melting at 76° to 77° C.

EXAMPLE 39 TO 91

The reactions are effected as in Example 8, whereby the following products are produced:

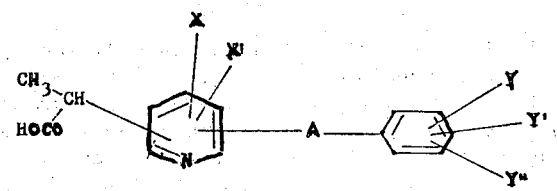

| Ex. No. | Position of CH$_3$'CH-COOH | X | X' | A | Y | Y' | Y'' | m.p.(° C) |
|---|---|---|---|---|---|---|---|---|
| 39 | 3 | H | H | 6-O | 3-Cl | H | H | 106–7 |
| 40 | 4 | H | H | 2-O | 4-CN | H | H | 105–6d |
| 41 | 4 | H | H | 2-O | 4-COOH | H | H | 154–6d |
| 42 | 4 | H | H | 2-O | 3-CF$_3$ | H | H | 155–7 Ca |
| 43 | 3 | H | H | 6-S | 4-Cl | H | H | 150 Ca |
| 44 | 4 | H | H | 2-O | 4-CONH$_2$ | H | H | 200–201 |
| 45 | 4 | H | H | 2-O | 4-OH | H | H | 187–9 Ca |
| 46 | 4 | H | H | 2-O | 4-AcO | H | H | 132.5–133.5 Ca |
| 47 | 3 | H | H | 6-O | 4-AcO | H | H | 145 Ca |
| 48 | 3 | H | H | 6-O | 4-OH | H | H | 205 Ca |
| 49 | 4 | H | H | 2-O | 4-NO$_2$ | H | H | 115–6d |
| 50 | 4 | H | H | 2-O | 4-NH$_2$ | H | H | 132–3d |
| 51 | 4 | H | H | 2-O | 4-AcNH | H | H | 142–3d |
| 52 | 4 | H | H | 2-O | 4-NH—COCC$_2$H$_5$ | H | H | 136–7d |
| 53 | 4 | H | H | 2-O | 4-NHCO—p-Ph-NH$_2$ | H | H | 206–8d |
| 54 | 3 | H | H | 6-O | 4-Br | H | H | 119–120 |
| 55 | 4 | H | H | 2-O | 3,4-Benzo | H | H | 138–9d |
| 56 | 3 | H | H | 6-O | 4-CN | H | H | 120–1 |
| 57 | 3 | H | H | 5-O | H | H | H | 135–135.5 |
| 58 | 3 | 4-Me | H | 6-O | H | H | H | 135–6 |
| 59 | 3 | 2-Me | H | 6-O | H | H | H | 92–3 |
| 60 | 3 | H | H | 6-O | 2-Me | 3-Me | H | 116–7 |
| 61 | 3 | H | H | 6-O | 2-Cl | H | H | 96–7 |
| 62 | 3 | H | H | 6-O | 2-Me | H | H | 65–7 |
| 63 | 3 | H | H | 6-O | 3-Me | H | H | 81–2 |
| 64 | 3 | H | H | 6-O | 3-Me | 5-Me | H | 120–1 |
| 65 | 3 | H | H | 6-O | 3-Me | 4-Me | H | 90–1 |
| 66 | 3 | H | H | 4-O | H | H | H | 145–6 |
| 67 | 3 | H | H | 6-O | 4-i-Bu | H | H | 77–8 |
| 68 | 4 | H | H | 2-O | 2-Me | 3-Me | H | 86–7d |
| 69 | 3 | 5-Me | H | 6-O | H | H | H | 107–8 |
| 70 | 3 | H | H | 6-O | 2-Me | 5-Me | H | 195 def. |

| | | Product | | | | | | |
|---|---|---|---|---|---|---|---|---|
| Ex. No. | Position of CH₃CHCOOH | X | X' | A | Y | Y' | Y'' | m.p.(° C) |
| 71 | 3 | H | H | 6-O | 2-Me | 4-Me | H | 189 def.Ca |
| 72 | 3 | H | H | 6-O | 2-Me | 6-Me | H | 202 def.Ca |
| 73 | 4 | H | H | 2-O | 3-Me | 4-Me | H | 123–4 d |
| 74 | 4 | H | H | 2-O | 3-Me | 5-Me | H | 103–4 d |
| 75 | 3 | H | H | 6-O | 2-Me | 3-Me | 5-Me | 128–9 |
| 76 | 3 | H | H | 6-O | 2-Me | 4-Me | 5-Me | 113–4 |
| 77 | 3 | H | H | 6-O | 3-Me | 4-Me | 5-Me | 155–6 |
| 78 | 3 | H | H | 6-O | 2-Me | 4-Me | 6-Me | 135–6 |
| 79 | 3 | H | H | 6-O | 3,4-(CH₂)₄- | | H | 169 def.Ca |
| 80 | 4 | H | H | 2-O | 2-Me | 3-Me | 5-Me | 125–6 d |
| 81 | 4 | H | H | 2-O | 3-Me | 4-Me | 5-Me | 126–7 d |
| 82 | 3 | H | H | 6-O | 2,3-(CH₂)₄- | | H | 165–6 def.Ca. |
| 83 | 3 | H | H | 6-O | 3,4-Benzo | | H | 120.5–121.5 |
| 84 | 3 | H | H | 6-O | 2,3-Benzo | | H | 131–2 |
| 85 | 3 | 4-Me | 5-Me | 6-O | H | H | H | 144–5 |
| 86 | 4 | 5,6-Benzo | | 2-O | H | H | H | 216–7 |
| 87 | 3 | 4,5-Benzo | | 6-O | H | H | H | 122–3 |
| 88 | 3 | 4,5-(CH₂) | | 6-O | H | H | H | 151–2 |
| 89 | 3 | H | H | 6-O | 3,4-(CH₂)₄ | | H | 122.5–123.5 |
| 90 | 3 | H | H | 6-O | 3-Met | H | H | 69.5–70.5 |
| 91 | 3 | 2-Me | 4-Me | 6-O | H | H | H | 218 d Ca |

Note: def. means "deformation".

EXAMPLE 92

Methyl 2-(2-p-chlorophenoxy-4-pyridyl)propionate (3.13 g) is treated with methyl iodide in the presence of 50 % sodium hydride in anhydrous tetrahydrofuran in a nitrogen atmosphere at room temperature for 1 hour and then at 40° C for 30 minutes, whereby methyl 2-(2-p-chlorophenoxy-4-pyridyl)isobutyrate (2.59 g) is obtained as crystals melting at 92° to 92.5° C. Then, this substance is treated with a mixture of 20 % aqueous potassium hydroxide and 95 % ethanol with refluxing for 10 minutes, whereby 2-(2-p-chlorophenoxy-4-pyridyl)isobutyric acid (2.35 g) is obtained as crystals melting at 135° to 136° C.

EXAMPLE 93 TO 94

Using diazopropane, the reaction is effected as in Example 8, whereby the following products are obtained:

2-(2-p-chlorophenoxy-4-pyridyl)-n-butyric acid, m.p. 92°–93° C;

2-(2-p-chlorophenoxy-5-pyridyl)-n-butyric acid aluminum complex, m.p. 236° C.

EXAMPLE 95 TO 97

Ethyl 2-(3-pyridyloxy-4-phenyl)propionate (1.05 g) is treated with m-chloroperbenzoic acid in methylene chloride at room temperature for 5 days, whereby ethyl 2-(3-pyridyloxy-4-phenyl)-propionate-N-oxide (1.10 g) is obtained. IR (CCl₄): 1745, 1215 cm⁻¹. This substance is then treated with a mixture of 20 % aqueous potassium hydroxide and 95 % ethanol at room temperature for 2 hours, whereby 2-(3-pyridyloxy-4-phenyl)-propionic acid-N-oxide (820 mg) is obtained as crystals melting at 139° to 140° C.

Similarly treated, the following products are obtained:

2-(2-phenoxy-5-pyridyl)propionic acid-N-oxide, m.p. 171°–172° C;

2-(2-phenoxy-4-pyridyl)propionic acid-N-oxide, m.p. 100°–101° C (decomp.).

We claim:

1. A compound selected from the group consisting of:

2-[4-(3-pyridyloxy)phenyl]propionic acid,
   2-(2-pyridyloxy-3-phenyl)propionic acid,
   2-[4-(5-bromo-2-pyridyloxy)phenyl]propionic acid,
   2-[4-(4-pyridyloxy)phenyl]propionic acid,
   2-[4-(4,5-dimethyl-2-pyridyloxy)phenyl]propionic acid,
   2-[4-(4-methyl-2-pyridyloxy)phenyl]propionic acid,
   2-(2-pyridyloxy-4-phenyl)propionic acid or alkali metal or alkali earth metal salts thereof.

2. A compound according to claim 1, namely, 2-[4-(3-pyridyloxy)phenyl]propionic acid or alkali metal or alkaline earth metal salts.

3. A compound according to claim 1, namely 2-(2-pyridyloxy-3-phenyl)propionic acid or alkali metal or alkaline earth metal salts.

4. A compound according to claim 1, namely 2-[4-(5-bromo-2-pyridyloxy)phenyl]propionic acid or alkali metal or alkaline earth metal salts.

5. A compound according to claim 1, namely 2-[4-(4-pyridyloxy)phenyl]propionic acid or alkali metal or alkaline earth metal salts.

6. A compound according to claim 1, namely 2-[4-(4,5-dimethyl-2-pyridyloxy)phenyl]propionic acid or alkali metal or alkaline earth metal salts.

7. A compound according to claim 1, namely 2-[4-(4-methyl-2-pyridyloxy)phenyl]propionic acid or alkali metal or alkaline earth metal salts.

8. A compound according to claim 1, namely 2-(2-pyridyloxy-4-phenyl)propionic acid or alkali metal or alkaline earth metal salts.

* * * * *